ns Patent [19]

United States Patent [19]
Malpass et al.

[11] 4,101,568
[45] Jul. 18, 1978

[54] PRODUCTION OF DIALKYLALUMINUM HYDRIDES

[75] Inventors: Dennis B. Malpass, LaPorte, Tex.; Spencer C. Watson, Wilmington, Del.

[73] Assignee: Texas Alkyls, Inc., Deer Park, Tex.

[21] Appl. No.: 661,913

[22] Filed: Feb. 27, 1976

[51] Int. Cl.² .............................................. C07F 5/06
[52] U.S. Cl. .............................................. 260/448 A
[58] Field of Search .................................. 260/448 A

[56] References Cited

U.S. PATENT DOCUMENTS

| | | | |
|---|---|---|---|
| 2,843,474 | 7/1958 | Ziegler et al. | 260/448 A X |
| 3,015,669 | 1/1962 | Ziegler et al. | 260/448 A |

OTHER PUBLICATIONS

Egger et al., Trans. Faraday Soc. V.67, 2629–2637, (1971).
Mole et al., Aus. J. Chem., 1964, v.17, pp. 310–314.
Mole et al., Organoaluminum Compounds, Elsevier Publ. Co., N.Y., p. 59, (1972).

Primary Examiner—Helen M. S. Sneed
Attorney, Agent, or Firm—Joel G. Ackerman

[57] ABSTRACT

Dialkylaluminum hydrides are produced by subjecting a mixed aluminum alkyl having the formula $$R_2AlR'$$

to pyrolysis. R is methyl, ethyl, n-alkyl or an alkyl group which has no hydrogen atoms on the carbon atom β to the aluminum. R' is an α- or β branched alkyl group having the formula

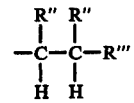

in which one R" is hydrogen and the other is alkyl and R'" is alkyl.

The mixed aluminum alkyl $R_2AlR'$ can be obtained either by reaction of two aluminum alkyls:

$$2R_3Al + R'_3Al \rightarrow 3R_2AlR'$$

or by reaction of a trialkylaluminum with a dialkylaluminum hydride:

$$2R_3Al + R'_2AlH \rightarrow 2R_2AlR' + R_2AlH,$$

in which case one third of the desired hydride is synthesized.

19 Claims, No Drawings

PRODUCTION OF DIALKYLALUMINUM HYDRIDES

BACKGROUND AND PRIOR ART

This invention relates to a process for preparation of dialkylaluminum hydrides. These compounds are known to be suitable co-catalysts in the polymerization of olefins and diolefins and as reducing agents for a variety of organic functional groups, in many cases with a great deal of stereospecificity in the final products.

A number of methods have been proposed or utilized for the preparation of dialkylaluminum hydrides; for example, by reduction of dialkylaluminum halides, by proportionation between a trialkylaluminum and aluminum hydride, by reaction of lithium aluminum hydride with trialkylboron compounds. Also, there have been proposed hydrogenolysis of trialkylaluminum compounds and reaction of trialkylaluminums with metallic aluminum in the presence of hydrogen. These processes all have drawbacks. For instance, reduction of dialkylaluminum halides with an alkali metal hydride is a slow reaction and can be exothermic. Additionally, the presence of solid by-products (alkali metal salts) can complicate product recovery. Aluminum hydride (for use in proportionation) is relatively unstable and may be contaminated with ether. Lithium aluminum hydride and trialkylboron compounds are quite expensive. Hydrogenolysis of trialkylaluminum compounds requires high pressures, for example, 200–300 atmospheres. Reaction of trialkylaluminum compounds with hydrogen in the presence of metallic aluminum requires the use of either activated aluminum or an external catalyst.

A simpler method of preparing some dialkylaluminum hydrides is described in U.S. Pat. No. 3,015,669 and involves subjecting trialkylaluminum compounds to thermal treatment, i.e., pyrolysis. The pyrolysis is conducted at temperatures of from 50° to 200° C, splitting off one molecule of olefin from the trialkylaluminum. Preferably, the trialkylaluminum contains at least one primary branched alkyl radical attached to the aluminum; apparently most preferably all three radicals attached to the aluminum are branched alkyls, and all compounds which were mentioned as being treated had all three radicals identical. It is stated that in many cases it is necessary, or at least advisable, to utilize a catalyst to promote splitting off of the olefin. This is particularly the case with triethylaluminum. Additionally, in the production of diethylaluminum hydride it is expedient not to allow the pyrolysis of the triethylaluminum to proceed to completion but to interrupt the reaction after approximately 50% conversion since the stability of the diethylaluminum hydride decreases as the triethylaluminum starting material is consumed.

Thus, the process of U.S. Pat. No. 3,015,669 is not fully satisfactory for the production of compounds such as diethylaluminum hydride and, by analogy, dimethylaluminum hydride. Additionally, this process is not considered satisfactory for the production of dialkylaluminum hydrides in which the carbon β to the aluminum atom does not have a hydrogen substituent, since the mechanism of hydride formation is known to involve transfer of a β-hydrogen atom to aluminum. Additionally, the general reaction of tri-n-alkylaluminums to produce the aluminum hydride plus an olefin proceeds rather slowly; it has also been found that the equilibrium lies more heavily on the side of the starting material than the products and that olefin elimination is complicated by addition of the carbon-aluminum bond of the trialkylaluminum to the olefin formed.

It is an object of the present invention to provide an improved process for the production of dialkylaluminum hydrides.

It is a further object of the present invention to provide a process for preparation of dialkylaluminum hydrides in which the carbon atom β to the aluminum atom is not substituted with hydrogen.

A further object of the present invention is to provide an improved process for the production of diethylaluminum hydride.

Another object of the present invention is to provide an improved process for the production of di-n-alkylaluminum hydrides.

Yet a further object of the present invention is to provide a process for the production of dialkylaluminum hydrides of relatively high purity and in relatively good yield.

A still further object of the present invention is to provide a process for the production of dialkylaluminum hydrides which does not require the presence of a catalyst.

Other objects and advantages of the invention will be apparent from the description which follows.

SUMMARY OF THE INVENTION

In brief, the invention herein comprises a process for the production of dialkylaluminum hydrides having the formula $$R_2AlH$$

in which R is methyl, ethyl, n-alkyl, or a trisubstituted  alkyl group having the formula

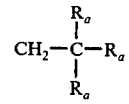

in which $R_a$ is an alkyl group, comprising heating a compound having the formula $$R_2AlR'$$

in which R' is an α- or β- mono-substituted alkyl group  of the type

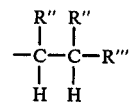

in which one R" is hydrogen and the other is alkyl and R'" is alkyl, at a temperature between about 50° and about 220° C.

DETAILED DESCRIPTION OF THE INVENTION

Essentially the invention comprises subjecting compounds of the type $R_2AlR'$ to a partial thermal pyrolysis to produce dialkylaluminum hydrides of the type $R_2AlH$. The compounds $R_2AlR'$ are readily produced from available materials by the reaction

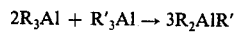

R is a methyl group, an ethyl group, an n-alkyl group such as n-propyl, n-butyl, n-pentyl, n-hexyl, n-heptyl, n-octyl, n-nonyl, n-decyl, etc., or a trisubstituted alkyl group of the type

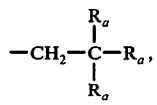

in which $R_a$ is an alkyl group, that is a trisubstituted alkyl group in which the carbon $\beta$ to aluminum has no hydrogen substituents. In general R may contain from 1 to 15, preferably from 1 to 5, carbon atoms. Examples of such groups are neopentyl, neohexyl, and analogous groups. The groups $R_a$ may be the same or different and preferably contain from 1 to 5 carbon atoms. R' represents an $\alpha$- or $\beta$- mono-substituted branched alkyl group, that is a group of the type

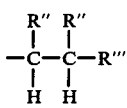

in which one R" is hydrogen and the other R" is an alkyl group, either straight chain or branched, and R''' is a straight chain or branched alkyl group. R" and R''' may be the same or different alkyl groups. Examples of groups fitting the definition of R' are isobutyl, sec-butyl, 2-methylbutyl, sec-amyl, 2-methylamyl, etc. R' may contain from 3 to 15, preferably from 3 to 5, carbon atoms. R" and R''' preferably contain from 1 to 5 carbon atoms.

In one embodiment the compounds $R_2AlR'$ are produced by mixing a trialkylaluminum with a dialkylaluminum hydride according to the reaction

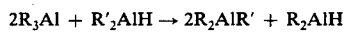

In the most preferred form, R' is isobutyl; thus the preferred starting material containing R' will be either triisobutylaluminum or diisobutylaluminum hydride, according to whichever method of preparing $R_2AlR'$ is utilized. Thus, in the preferred form, the process involves the pyrolysis of compounds having the formula

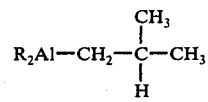

(that is, one R" is hydrogen, the other is methyl, and R''' is methyl). The pyrolysis is conducted without utilizing a catalyst, at a temperature between about 50° and 220° C until the isobutyl groups are largely converted to hydride sites by cracking off isobutylene. In such a process no special activation of the starting materials (which are commercially available) is necessary.

The amount of time required for the reaction depends on the reaction system and the nature of R. For example, pyrolysis of dimethylisobutylaluminum requires a more lengthy reaction period than the corresponding diethyl compound under similar conditions. In general, it is preferable, though not necessary, to pass an inert gas through the liquid while it is heated in order to permit rapid removal of the generated olefin and consequently prevent back-reaction of the olefin with the hydride product. This also permits the reaction to be carried out over a shorter time period.

It is most convenient to conduct the pyrolysis process under an atmospheric pressure of an inert gas such as helium, argon or nitrogen; the process may also be carried out under sub- or super-atmospheric pressures. This may be advantageous in some cases. For example, pyrolysis of diethyl compounds may proceed more smoothly at reduced pressures. Conversely, pyrolysis of dimethyl compounds may be facilitated by conducting the process under super-atmospheric temperatures up to about 15 atmospheres in order to attain higher liquid temperatures (reaction temperatures at atmospheric pressure are limited to about 128°–154° C because of the relatively low boiling points of both trimethylaluminum and dimethylaluminum hydride). If the reaction is to be carried out at super-atmospheric pressure, provision should be made for removal of the olefin by-product to prevent back-reaction.

As will be seen from the examples which follow, the process of the present invention provides a method for facilitating production of diethylaluminum hydride and dimethylaluminum hydride in either better yield, higher purity, or less complicated a fashion than the pyrolysis process of U.S. Pat. No. 3,015,669. Furthermore, it provides a method for producing dialkylaluminum hydrides in which the carbon atom $\beta$ to the aluminum atom is not substituted with hydrogen. Such compounds connot be produced by pyrolysis of the corresponding alkylaluminum substituted with three alkyl groups of the same type according to the process of the said patent.

The following examples are illustrative of the invention.

EXAMPLE 1

To a nitrogen-purged one-liter three-necked flask equipped with a reflux condenser, thermometer well, and magnetic stirring bar were added 285.7 g (2.502 mole) of triethylaluminum and 248.8 g (1.255 mole) of triisobutylaluminum. A small exotherm (ca 10° C) was noted upon mixing. Analysis of the resultant diethylisobutylaluminum showed 19.08% aluminum and gas chromatographic analysis of the hydrolysis gases showed 61.94 mole % ethane and 31.56 mole % isobutane, the remainder being small amounts of methane, propane, n-butane, isobutylene, and hydrogen (theoretical values for this compound: 18.97% aluminum and 66.67 mole % ethane and 33.33 mole % isobutane in the hydrolysis gases).

A total of 148.3 g (1.043 mole) of diethylisobutylaluminum prepared above was charged to a 250-ml three-necked flask equipped with a reflux condenser, thermometer well, sparge tube with fritted glass tip, and magnetic stirring bar. This material was sparged with dry nitrogen for 8 hours at 124°–139° C after which analysis showed 25.97% aluminum and 60.56 mole % ethane, 10.08 mole % isobutane and 27.51 mole % hydrogen. After sparging and heating at 174°–189° C for an additional six hours, these values were 27.77% aluminum, 58.70 mole % ethane, 6.61 mole % isobutane, and 32.20 mole % hydrogen. This product corresponds to approximately 90 mole % diethylaluminum hydride and 10 mole % diisobutylaluminum hydride. Although there was a gray precipitate coating the walls of the flask and diptube, the crude product was clear and colorless and was isolated in about 95% yield.

The crude product was distilled at reduced pressure (0.1–0.2 mm Hg) and 55.0 g (61%) of a clear, colorless mobile liquid was obtained. Analysis showed the distillate to contain 29.29% aluminum and 63.92 mole % ethane, 2.55 mole % isobutane, and 32.47 mole % hydrogen in the hydrolysis gases or approximately 96 mole % diethylaluminum hydride and 4 mole % diisobutylaluminum hydride.

EXAMPLE 2

Using the same diethylisobutylaluminum prepared in Example 1, another preparation of diethylaluminum hydride was performed on a larger scale. The same experimental procedure as Example 1 was employed except that heating and sparging were carried out for 11 hours at 141°–154° C. The crude product was approximately 88 mole % diethylaluminum hydride and 12 mole % diisobutylaluminum hydride. A quantitative yield of crude material was obtained. This material was subjected to vacuum distillation through a 2-ft. vacuum-jacketed, silvered column (packed with stainless steel protruded packing) and a partial take-off distilling head. Two fractions were taken. Analysis of Fraction A (b.p. 47°–50° C 0.4 mm Hg) showed 27.28% aluminum, and 81.03 mole % ethane, 0.07 mole % isobutane and 17.57 mole % hydrogen in the hydrolysis gases. Fraction A corresponded to a 1:1 molar mixture (complex) of triethylaluminum and diethylaluminum hydride. Analysis of Fraction B (b.p. 70–73 0.7–0.8 mm Hg) showed 30.94% aluminum, and 66.86 mole % ethane, 0.05 mole % isobutane, and 33.07 mole % hydrogen. Thus, Fraction B is 99% pure diethylaluminum hydride. The overall yield of diethylaluminum hydride in both fractions was 55%.

EXAMPLE 3

To the usual apparatus were charged 304.4 g (2.666 mole) of triethylaluminum and 191.2 g (1.344 mole) of diisobutylaluminum hydride. This mixture was sparged with dry nitrogen (rate = 1.5 l/minute) at 170°–190° C for six hours. Analysis of the resultant crude gray product showed 28.38% aluminum and 61.68 mole % ethane, 5.98 mole % isobutane and 30.98 mole % hydrogen in the hydrolysis gases. This corresponds to approximately 91 mole % diethylaluminum hydride and most of the remainder diisobutylaluminum hydride. The yield of crude material was 343 g (99%). The gray appearance (probably caused by finely divided elemental aluminum) can be removed by filtration or centrifugation to produce a clear, colorless liquid.

A total of 327.2 g of crude material was subjected to vacuum distillation through an apparatus similar to that used in Example 2 except that a 1-ft. vacuum-jacketed Vigreaux column was used in place of the packed column. Two fractions were collected. The first fraction (76.8 g) contained 27.54% aluminum and 73.25 mole % ethane, 1.22 mole % isobutane and 23.71 mole % hydrogen in the hydrolysis gases. This corresponds approximately to a 70:30 molar mixture of diethylaluminum hydride and triethylaluminum. The second fraction (159.9 g) contained 30.46% aluminum and 62.94 mole % ethane, 2.66 mole % isobutane and 34.04 mole % hydrogen or 96 mole % diethylaluminum hydride and 4% diisobutylaluminum hydride and triethylaluminum. The total yield of both fractions (236.7 g) amounts to a 72% overall yield adjusted for the quantity of crude charged for distillation.

EXAMPLE 4

A total of 295 g (4.093 mole) of trimethylaluminum was added to 302.9 g (2.130 mole) of diisobutylaluminum hydride. Analysis of the resultant product showed 27.75% aluminum and 64.34 mole % methane, 22.40 mole % isobutane, and 12.70 mole % hydrogen in the hydrolysis gases. In the usual apparatus, this material was heated at 145°–155° C for about 35 hours. Occasionally, dry nitrogen was sparged through the liquid to facilitate removal of isobutylene from the system. After this period of heating, a total of 428.6 g of crude material was isolated which contained 33.80% aluminum and 62.44 mole % methane, 12.47 mole % isobutane, and 24.65 mole % hydrogen.

Distillation of the crude reaction product gave five fractions. The combined yield of dimethylaluminum hydride from these fractions was 53%. The purities ranged from 50 to 95% with the main contaminant in the early fractions being trimethylaluminum, while the main contaminant in the later fractions was diisobutylaluminum hydride. The fractions which were largely dimethylaluminum hydride were very viscous, clear liquids.

EXAMPLE 5

A mixture consisting of 2 mole-equivalents of tri-n-butylaluminum and one mole-equivalent of diisobutylaluminum hydride is heated and sparged with nitrogen to give crude di-n-butylaluminum hydride.

EXAMPLE 6

Following the same general procedure used in the previous examples, a sample of n-octylisobutylaluminum is heated and sparged with nitrogen. Crude di-n-octylaluminum hydride is obtained.

EXAMPLE 7

To 360.8 g (1.501 mole) of trineopentylaluminum is added a total of 151.1 g (0.762 mole) of triisobutylaluminum. This material is heated and sparged with nitrogen in the usual manner. The resultant product contains dineopentylaluminum hydride.

What is claimed is:

1. A non-catalytic process for the production of dialkylaluminum hydrides having the formula $R_2AlH$ in which R is an n-alkyl group having from 1 to 15 carbon atoms or a tri-substituted alkyl group having the formula

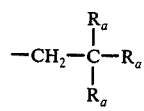

in which $R_a$ is an alkyl group, comprising heating a compound having the formula $R_2AlR'$ in which $R'$ is an α- or β- mono-substituted alkyl group of the type

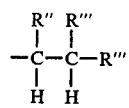

in which one $R''$ is hydrogen and the other is alkyl and $R'''$ is alkyl, at a temperature between about 50° and about 220° C.

2. A process according to claim 1 in which $R_2AlR'$ is formed by mixing a compound having the formula $R_3Al$ with a compound having the formula $R'_3Al$ in a mole ratio of $R_3Al : R'_3Al$ of about 2:1.

3. A process according to claim 1 in which $R_2AlR'$ is formed by mixing a compound having the formula $R_3Al$ with a compound having the formula $R'_2AlH$ in a mole ratio of $R_3Al : R'_2AlH$ of about 2:1.

4. A process according to claim 1 in which R is methyl.

5. A process according to claim 1 in which R is ethyl.

6. A process according to claim 1 in which R is an n-alkyl group having from 3 to 15 carbon atoms.

7. A process according to claim 6 in which R is n-butyl.

8. A process according to claim 6 in which R is n-octyl.

9. A process according to claim 1 in which R is a tri-substituted alkyl group having the formula

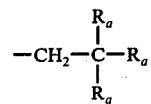

10. A process according to claim 9 in which R is neopentyl.

11. A process according to claim 1 in which R' is isobutyl.

12. A process according to claim 1 in which olefinic product is continuously removed during the process.

13. A process according to claim 12 in which the olefinic product is removed by passing an inert gas through the reaction mixture.

14. A process according to claim 1 in which the temperature is between about 80° and about 190° C.

15. A process according to claim 1 carried out at sub-atmospheric pressure.

16. A process according to claim 1 carried out at super-atmospheric pressure.

17. A process according to claim 16 in which the pressure is between about 1 and about 15 atmospheres.

18. A process according to claim 1 further comprising purifying the dialkylaluminum hydride by distillation under reduced pressure.

19. A process according to claim 1 in which R contains from 1 to 5 carbon atoms.

* * * * *